United States Patent
Larsen

(10) Patent No.: US 9,877,479 B2
(45) Date of Patent: Jan. 30, 2018

(54) PAMOIC ACID BLOCKS ETHELYNE SIGNALING

(71) Applicant: THE REGENTS OF THE UNIVERSITY OF CALIFORNIA, Oakland, CA (US)

(72) Inventor: Paul Brian Larsen, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/149,899

(22) Filed: May 9, 2016

(65) Prior Publication Data

US 2016/0262387 A1 Sep. 15, 2016

Related U.S. Application Data

(63) Continuation of application No. 14/309,478, filed on Jun. 19, 2014, now abandoned, which is a continuation of application No. 13/231,590, filed on Sep. 13, 2011, now abandoned.

(60) Provisional application No. 61/382,791, filed on Sep. 14, 2010.

(51) Int. Cl.
*A01N 37/40* (2006.01)
*A01N 37/44* (2006.01)
*A01N 3/02* (2006.01)

(52) U.S. Cl.
CPC .............. *A01N 37/40* (2013.01); *A01N 3/02* (2013.01); *A01N 37/44* (2013.01)

(58) Field of Classification Search
CPC ........... A01N 37/40; A01N 3/02; A01N 37/44
See application file for complete search history.

(56) References Cited

U.S. PATENT DOCUMENTS

| | | | |
|---|---|---|---|
| 3,901,686 | A | 8/1975 | Alt |
| 3,917,838 | A | 11/1975 | Bass et al. |
| 4,451,466 | A | 5/1984 | Horne et al. |
| 5,521,192 | A | 5/1996 | Henrie, II et al. |
| 2009/0054237 | A1 | 2/2009 | Harrison et al. |

FOREIGN PATENT DOCUMENTS

WO 98/32423 A1 7/1998

OTHER PUBLICATIONS

Leon-Reyes et al.; "Ethylene signaling renders the jasmonate response of *Arabidopsis* insensitive to future suppression by salicylic acid"; *Mol. Plant-Microbe Interact.*; 23(2):187-197 (2010).
Leslie et al.; "Inhibition of ethylene biosynthesis by salicylic acid"; *Plant Physiol.*; 88(3):833-837 (1988).
Raskin, I.; "Salicylate, a new plant hormone"; *Plant Physiol.*; 99(3):799-803 (1992).
Singh et al.; "The relation of chemical structure to biological activity in certain organic compounds"; *The Indian Journal of Horticulture*; 13(3):109-140 (1956).
Singh et al.; "Activity in certain organic compounds on the abscission"; *The Indian Journal of Horticulture*; 13(4):165-180 (1956).
The International Search Reporta nd Written Opinion from PCT/US2011/051649, dated Apr. 30, 2012.
The Supplementary European Search Report from EP 11825899.5, dated Mar. 14, 2014.

*Primary Examiner* — John Pak
*Assistant Examiner* — Andriae M Holt
(74) *Attorney, Agent, or Firm* — Kilpatrick Townsend & Stockton LLP

(57) ABSTRACT

The disclosure provides methods and compositions for modulating ethylene and auxin signaling and ethylene production in plants.

3 Claims, 14 Drawing Sheets

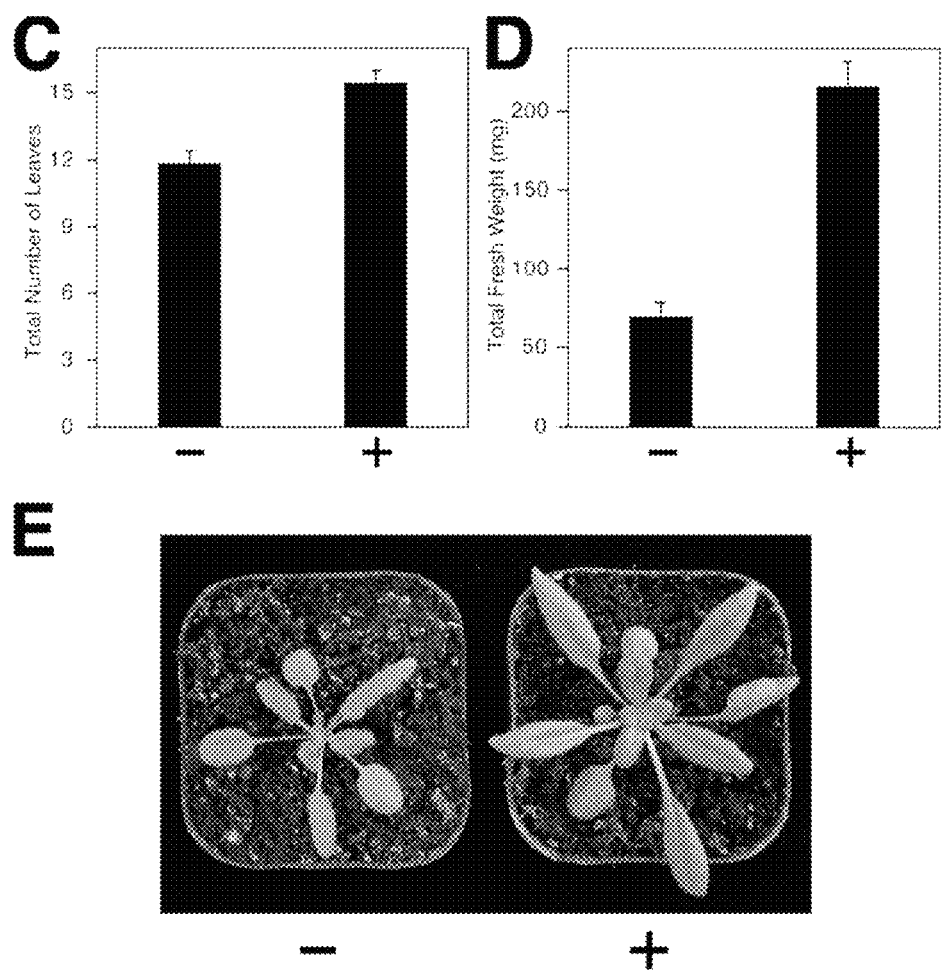
Figure 4C-E

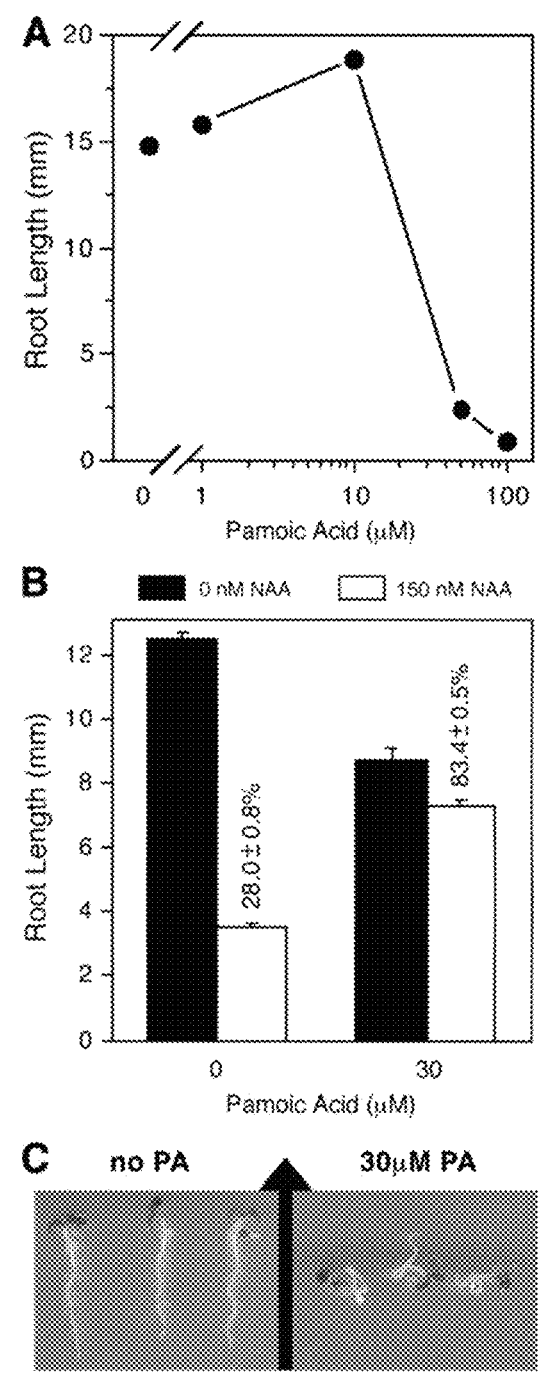
Figure 10A-C

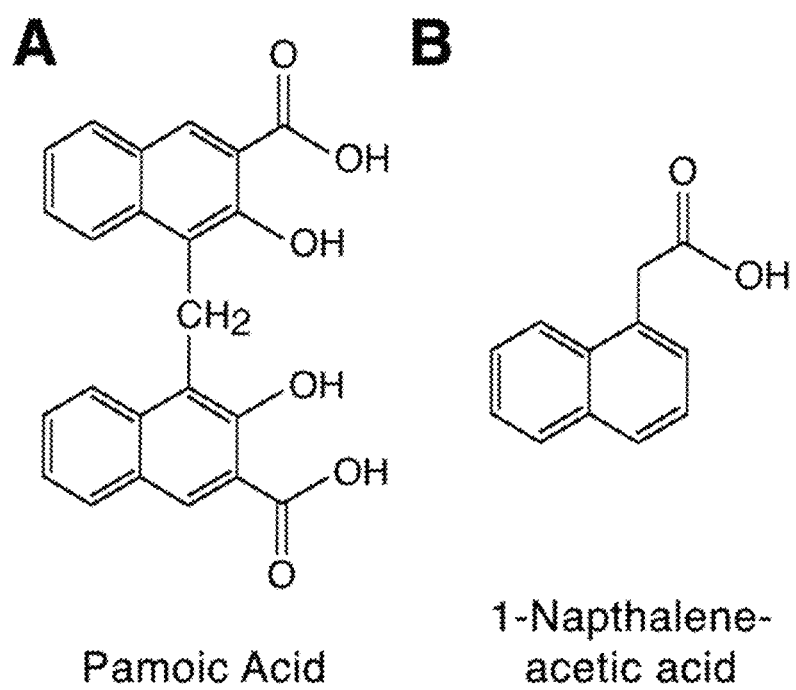
Figure 11A-B

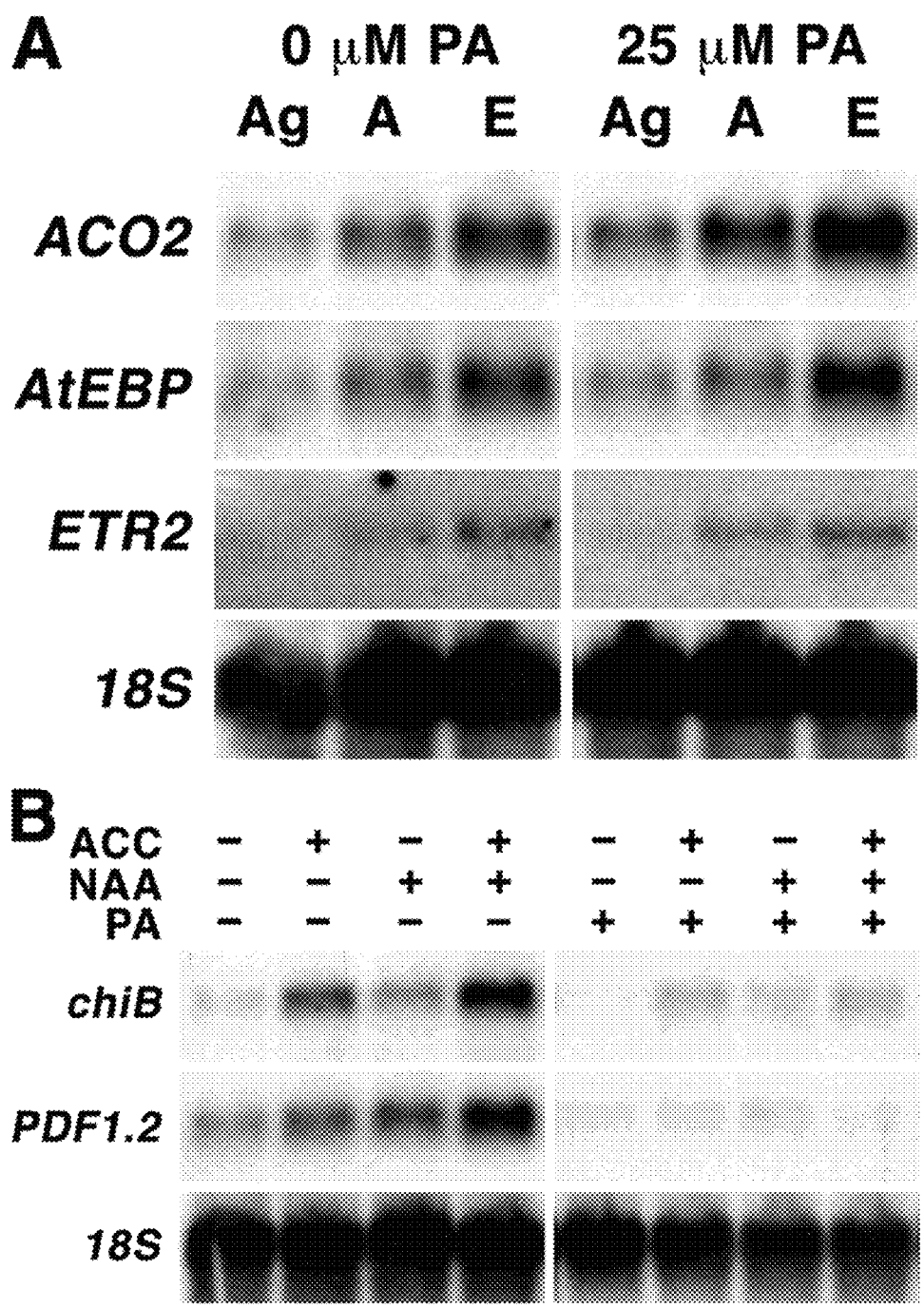
Figure 12A-B

PAMOIC ACID BLOCKS ETHELYNE SIGNALING

CROSS REFERENCE TO RELATED APPLICATIONS

This application is a continuation of U.S. patent application Ser. No. 14/309,478, filed Jun. 19, 2014, which is a continuation of U.S. patent application Ser. No. 13/231,590 filed Sep. 13, 2011, now abandoned, which claims priority to U.S. Provisional Application Ser. No. 61/382,791 filed Sep. 14, 2010, the disclosures of which are incorporated herein by reference.

TECHNICAL FIELD

The disclosure provides methods and compositions for modulating ethylene signaling and ethylene production in plants.

BACKGROUND

Ethylene ($C_2H_4$) is a gaseous plant hormone that affects myriad developmental processes and fitness responses in plants, such as germination, flower and leaf senescence, fruit ripening, leaf abscission, root nodulation, programmed cell death, and responsiveness to stress and pathogen attack (Johnson, P. R. and Ecker J. R., Annu Rev Genet. 32, 227-254, 1998). Another effect of ethylene on plant growth is the so-called triple response of etiolated dicotyledoneous seedlings. This response is characterized by the inhibition of hypocotyl and root cell elongation, radial swelling of the hypocotyl, and exaggerated curvature of the apical hook. Over the past decade, genetic screens based on the triple response phenotype have identified more than a dozen genes involved in the ethylene response in plants. These genes can be divided into three distinct categories: constitutive triple response mutants (eto1, eto2 and eto3, ctr1 and ran1/ctr2); ethylene insensitive mutants (etr1, etr2, ein2, ein3, ein4, ein5, and ein6); and tissue-specific ethylene insensitive mutants (hls1, eir1, and several auxin resistant mutants).

SUMMARY

The disclosure provides chemical, small molecule agents useful in inhibiting ethylene signaling in plants and in some embodiments, ethylene production. Pamoic acid and derivatives are provided that are capable of reversing the constitutive ethylene response of ctrl-3 mutants, demonstrating that pamoic acid blocks etheylen signaling at a point downstream of the negative regulator, CTR1. Regulation of ethylene dependent phenomena is extremely important for several horticultural crops including all climacteric fruits such as tomato and avocado, along with issues such as determination of femal vs. male flowers in cucurbits. Pamoic acid and derivatives thereof provide a useful approach for controlling ethylene through ethylene signaling.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

FIGS. 4A-E. Wild type *Arabidopsis* plants were grown in soil under constant lighting for 5 weeks in the presence of either 0 or 10 µM pamoic acid. The chemical was administered by repeated bottom watering over the course of the experiment. Following this, total leaf area (A), area of the largest leaf (B), total leaf number (C) and total fresh weight (D) were determined for each treatment (n=5).

FIGS. 10A-C shows graphs depicting the growth of seelings on increasing amount sof palmoic acid (PA). (A) shows that high concentrations of PA almost completely block root growth. (B) shows seedling were grown in the absence or presence of a highly inhibitory amount of 1-Napthalene-acetic acid (NAA), a subset of these seedlings also had PA added to them. (C) shows that treatment of wild-type roots with PA completely destroys the gravitropic response of seedling roots.

FIGS. 11A-B shows the chemical structure of PA and a synthetic auxin known as NAA.

FIGS. 12A-B shows the effects of PA on gene expression. (A) shows that ethylene inducible genes normally upregulated following ethylene treatment are also upregulated in the presence of PA. (B) shows gene expression of genes dependent on auxin and theylen in to presence of PA.

DETAILED DESCRIPTION

Figure 1:
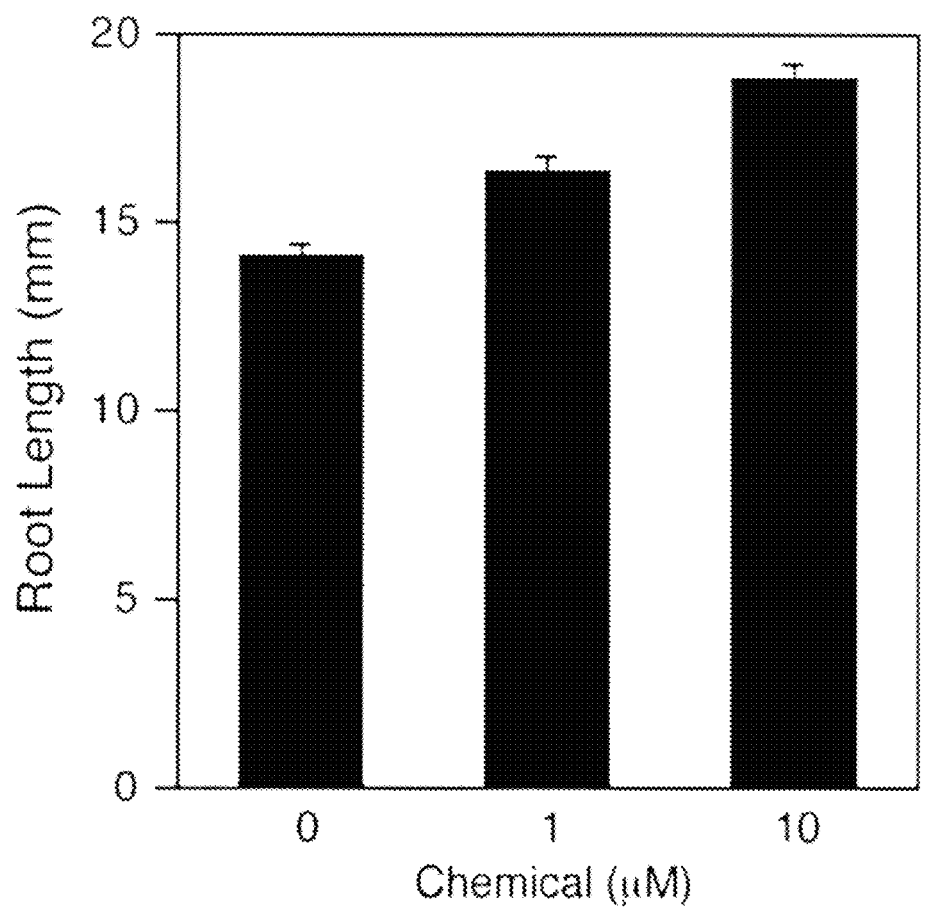
FIG. 1. Wild type *Arabidopsis* seedlings were grown in the light in nutrient medium supplemented with 0, 1, or 10 µM pamoic acid for 7 days. Following this, roots of each were measured (n=40).
Figure 2:
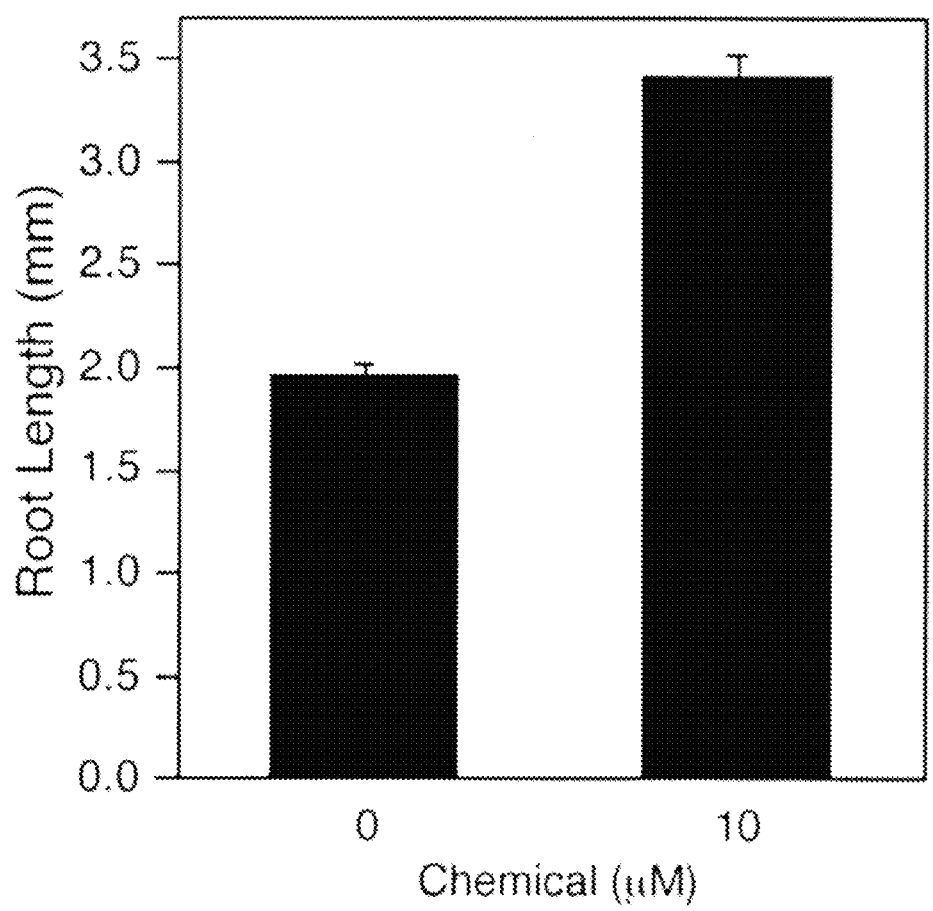
FIG. 2. Wild type *Arabidopsis* seedlings were grown in saturating ethylene (100 ppm) in the light in nutrient medium supplemented with either 0 or 10 µM pamoic acid for 7 days. Following this, roots of each were measured (n=40).
Figure 3:
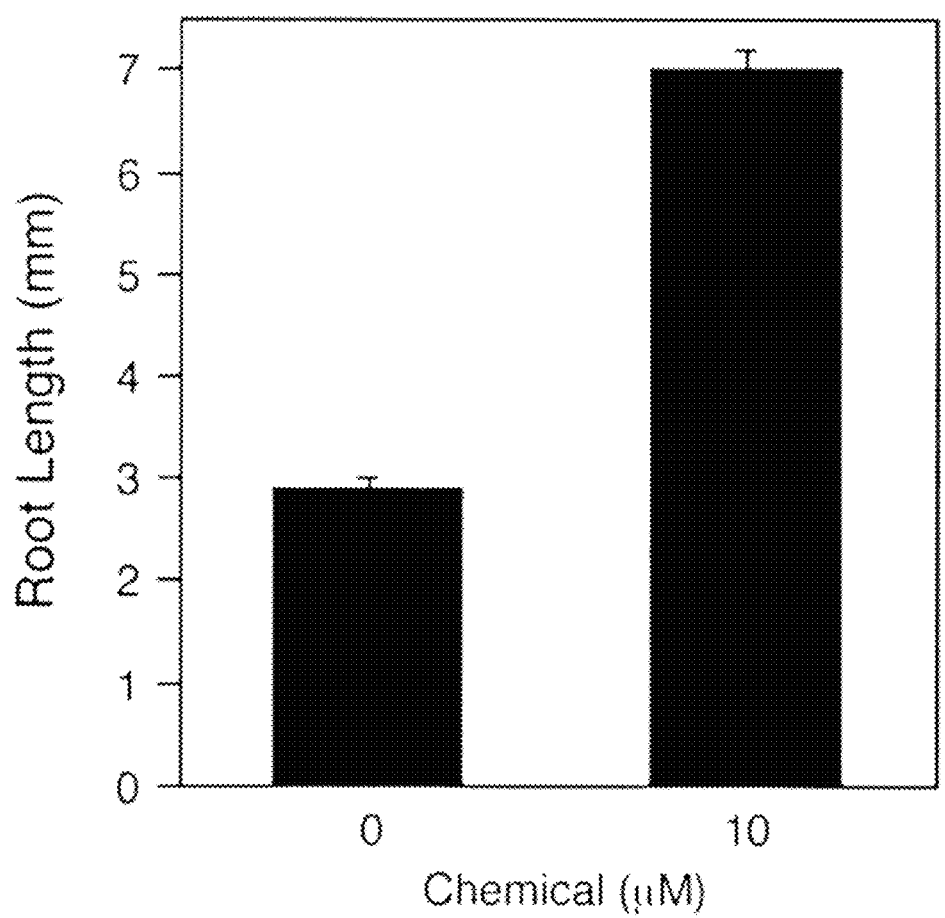
FIG. 3. Mutant *Arabidopsis* seedlings (ctrl-3) that have a constitutive ethylene response phenotype, including severe root shortening dependent on unregulated ethylene signaling, were grown in the light in nutrient medium supplemented with either 0 or 10 µM pamoic acid for 7 days. Following this, roots of each were measured (n=40).
Figure 4A:
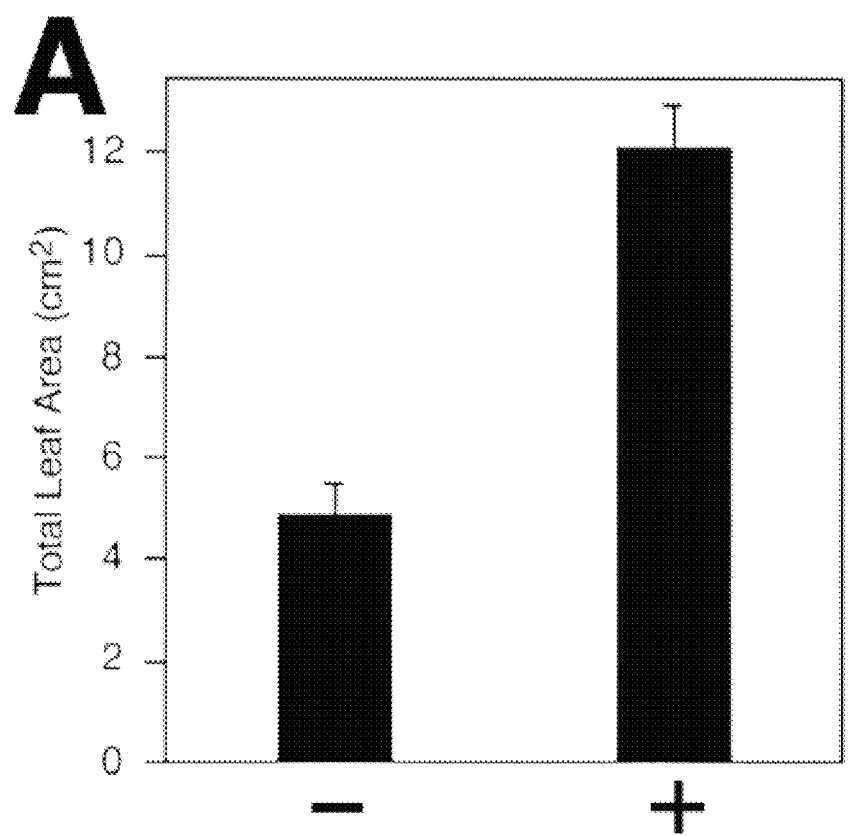
Figure 4B:
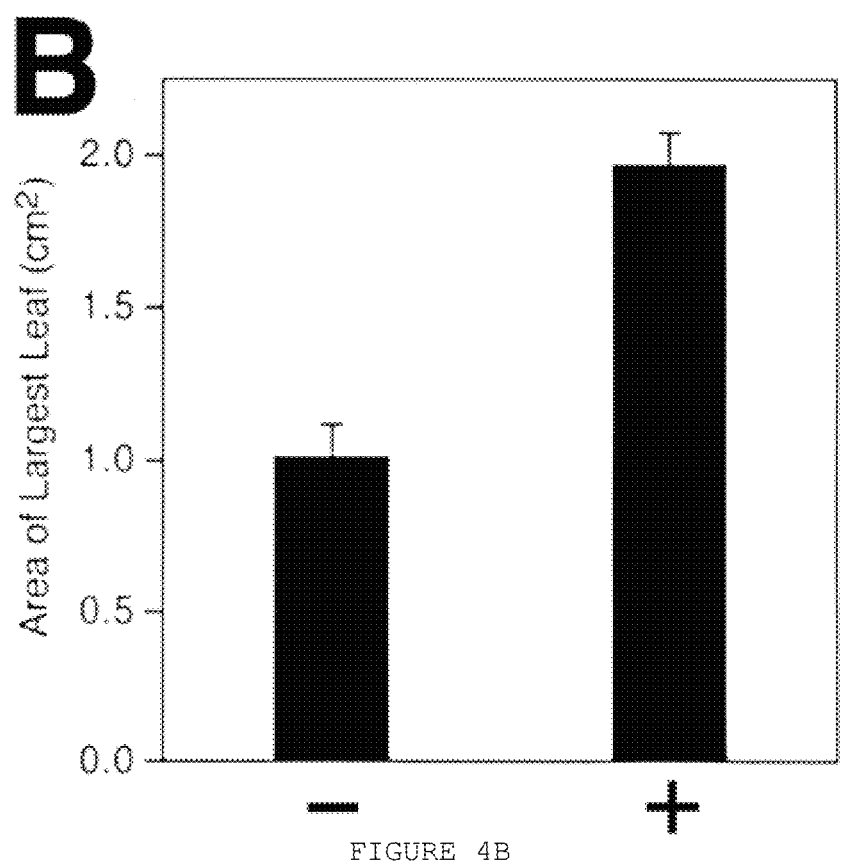

As used herein and in the appended claims, the singular forms "a," "and," and the include plural referents unless the context clearly dictates otherwise. Thus, for example, reference to "a substrate" includes a plurality of such substrates and reference to "the cell" includes reference to one or more cells and equivalents thereof.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Ethylene causes developmental changes that result in fruit ripening through the production of enzymes including, but not limited to, hydrolases to facilitate break down of fruit components, amylases to accelerate hydrolysis of starch into sugar, pectinases to catalyze degradation of pectin, and so on. Ethylene increases the transcription of genes that are then transcribed and translated to make these enzymes. The enzymes then catalyze reactions to alter the characteristics of the fruit.

Enzymes produced as a result of exposure to ethylene facilitate the ripening responses. Chlorophyll is broken down and pigments are made so that the fruit skin changes color from green to red, yellow, or blue. Acids are broken down so that the fruit changes from sour to neutral. The degradation of starch by amylase produces sugar. This reduces the mealy (floury) quality and increases juiciness of the fruit. The breakdown of pectin by pectinase results in a softer fruit. Enzymes also break down large organic molecules into volatile smaller molecules which are detected as an aroma.

Fruit drop is related to fruit ripening. The fruit-ripening process described above, also occurs in a layer of cells in the pedicel near the point of attachment to the stem of the plant. This layer of cells in the pedicel is often called the abscission zone because this layer will eventually separate and the fruit will drop from the plant.

The cells in this cross sectional layer in the pedicel receive the ethylene signal from the ripening fruit. Reception of the signal results in the production of new enzymes. The cells "ripen" and pectinases attack the cells of the abscission zone. When the cell connection have been sufficiently weakened, the weight of the fruit will cause it to fall from the plant.

Plant senescence is a genetically programmed process; it is the last phase of plant development and ultimately leads to death. Plant hormones such as ethylene, auxins and cytokinins play vital roles in the regulation of senescence.

Auxins are well-known plant growth or development hormones, that were first extensively studied in the mid 1930's. Auxins are involved in a variety of plant activities although their ability to promote cell elongation is perhaps best known. The most widely occurring, natural auxin in indole-3-acetic acid (IAA). It occurs in both free and conjugated states in plants and seeds. Early on, the use of IAA was shown to be advantageous in stimulating root formation in plant cuttings. Subsequently, synthetic materials such as indole-3-butyric acid (IBA) and naphthleneacetic acid (NAA) were found to be even more useful at least in part, due to their greater stability. Most recently it has been found that IBA also occurs naturally in some plants albeit at very low levels. Today IBA and NAA are widely used as synthetic rooting hormones. They are most often applied to the base of plant (stem and leaf) cuttings, and to transplantings since it is known that auxins are required for initiation of adventitious roots on stems, and to stimulate root growth in general. Rooting hormones are widely used for plant propagation because they hasten root initiation, improve rooting percentages, produce more uniform rooting, and increase the number and quality of roots. As used herein, the term "auxin" refers to a class of phytohormone or plant growth regulators that control cell expansion. Auxins include indole-3-acetic acid, indoleacetic acid, or, IAA; see, e.g., Bennett (1998) Philos. Trans. R. Soc. Lond. B. Biol. Sci. 353:1511-1515; Guilfoyle (1998) Plant Physiol. 118(2):341-347, for further details on the structure and physiology of auxins.

As used herein, the term "plant" refers to either a whole plant, a plant part, a plant cell, or a group of plant cells, such as plant tissue, for example. Plantlets are also included within the meaning of "plant". Plants include flowering, decorative plants, agricultural plant and the like.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, potato, rapeseed, field beans, soybeans, peppers, lettuce, peas, alfalfa, clover, cole crops or Brassica oleracea (e.g., cabbage, broccoli, cauliflower, brussels sprouts), radish, carrot, beets, eggplant, spinach, cucumber, squash, melons, cantaloupe, sunflowers and various ornamentals. Woody species include poplar, pine, sequoia, cedar, oak, etc.

The disclosure provides methods and compositions for inhibiting auxin and ethylene signaling in a plant comprising contacting a plant, plant part, tissue, flower, fruit and the like with a pamoic acid or derivative thereof. Such methods and compositions are useful to inhibit fruit ripening and flowering. For example, the methods and compostions of the disclosure can be used as a stabilizer or preservative for fruits and flowers.

The disclosure also provide a method of inhibiting ethylene production or auxin induced gene expression in a plant comprising contacting the plant with a pamoic acid or derivative thereof.

The disclosure provides a method of inhibiting senescence due to ethylene production in a plant comprising contact the plant with a Pamoic acid or derivative thereof.

The disclosure also provides compositions useful in the methods of the disclosure.

Methods are provided for modulating ethylene signaling and/or auxin induced gene expression in a plant or inhibiting ethylene production comprising applying or contacting a plant with an effective amount of a composition comprising pamoic acid or derivative thereof. "Effective amount" is intended to mean an amount sufficient to inhibit ethylene production or inhibit gene expression associated with auxin or an auxin agonist.

The methods and compositions of the disclosure can be employed to modify a variety of different ethylene responses such as, for example, the ripening and/or senescence of flowers, fruits, and vegetables; abscission of foliage, flowers, and fruit; the life of ornamentals such as potted plants, cut flowers, shrubbery, seeds, and dormant seedlings; auxin activity, terminal growth, apical dominance, branching, tillering, morphology of plants, modifying the susceptibility to plant pathogens such as fungi, changing bio-chemical compositions of plants, abortion or inhibition of flowering and seed development, lodging effects, seed germination and dormancy, and hormone or epinasty effects.

Pamoic acid, also called embonic acid is a naphthoic acid derivative. Salts and esters of pamoic acid are known as pamoates. It can be prepared by the reaction of 2-hydroxy-3-naphthoic acid with formaldehyde. In pharmacology, the ester form of pamoic acid (pamoate ion) that can be used as a counter ion of a drug compound to increase the solubility of the drug in water. Pamoic acid has the general structure/formula I:

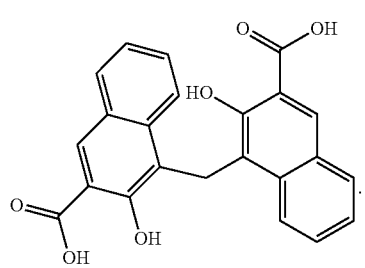
(I)

Derivatives of pamoic acid useful in the disclosure can have a general structure (II):

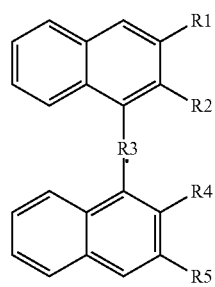

In one embodiment, $R_1$ and $R_5$ are —COOCH$_2$C$_6$H$_5$; $R_2$ and $R_4$ are —OH; $R_3$ is —CH$_2$—. In another embodiment, $R_1$ and $R_5$ are —COOCH(CH$_3$)$_2$; $R_2$ and $R_4$ are —OH; $R_3$ is —CH$_2$—. In another embodiment, the compound of formula (II) can be described generally as:

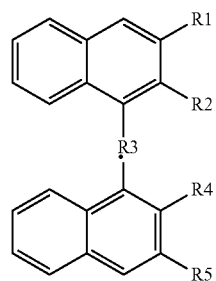

wherein $R_1$ and $R_5$, which may be the same or different, are COOR6, CONHR$_6$, SO$_2$R$_6$, SO$_2$NHR$_6$, SO$_3$R$_6$, OR$_6$, COR$_6$, NHR$_6$, in which $R_6$ is H or a straight or branched, saturated or unsaturated alkyl chain, with from 1 to 5 carbon atoms, or phenyl, substituted by $R_7$; in which $R_7$ is OH, COOH, SO$_3$H, NR$_8$R$_9$,

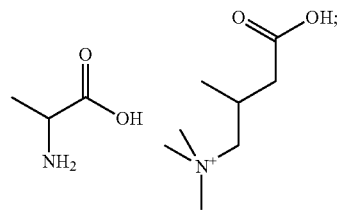

in which $R_8$ and $R_9$, which may be the same or different, are H, alkyl with 1 to 5 carbon atoms; $R_2$ and $R_4$, which may be the same or different, are H, OH, NHR$_6$, OCO—R$_{10}$—NR$_8$R$_9$,

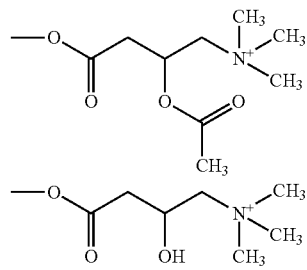

in which $R_{10}$ is a straight or branched, saturated or unsaturated alkyl chain with from 1 to 5 carbon atoms; $R_3$ is —(CH$_2$)$_n$—, —CH$_2$—O—, —CH(R$_{11}$)—, wherein n is an integer from 1 to 4; $R_{11}$ is a straight or branched alkyl with from 1 to 5 carbon atoms, substituted by an amino group, alkylamino C$_1$-C$_5$, dialkylamino C$_1$-C$_5$, OH, alkyloxy C$_1$-C$_5$.

The disclosure provides method of modulating ethylene signaling or auxin-induced processes in plants comprising contacting a plant with a Pamoic acid or derivative thereof.

The compositions of the disclosure include a pamoic acid or derivative thereof and may further include a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular plants. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the disclosure are normally applied in the form of compositions and can be applied to the crop area, plant, or seed to be treated or in the case of cuttings (e.g., cut flowers) to the water. For example, the compositions of the disclosure may be applied during growth, seeding or storage.

The Pamoic acid or derivative thereof of the disclosure may be applied simultaneously or in succession with other compounds. Methods of applying a composition of the disclosure include, but are not limited to, foliar application, seed coating, and soil or water application. The number of applications and the rate of application depend on the particular purpose and plant (e.g., to preserve cut flowers, of inhibit fruit spoilage).

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphthalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the disclosure can be in a suitable form for direct application or as a concentrate of primary composition that requires dilution with a suitable quantity of water or other diluant before application. The concentration of Pamoic acid or derivative thereof will vary depending upon the nature of the particular formulation, specifically, whether it is a concentrate or to be used directly.

A composition of the disclosure can be applied to the environment of a plant, for example, spraying, atomizing, dusting, scattering, coating or pouring, introducing into or on the soil, introducing into irrigation water, by seed treatment or general application or dusting. It is generally important to modulate ethylene signaling and production during periods when ethylene production is high, as this is the time when the plant can be most severely damaged. The compositions of the disclosure can conveniently contain an insecticide if this is thought necessary.

The disclosure is illustrated in the figures, which are provided by way of illustration and are not intended to be limiting.

Experiments were performed to show that auxin inducible gene expression is reduced or eliminated by PA treatment. The effects of auxin on an auxin inducible reporter gene called DR5 were measured. Normally, auxin treatment results in increased expression of DR5, which is evidenced by blue color in the roots and leaf tip. PA treatment, especially at high levels, reduced or eliminated DR5 expression. This is compared to a known anti-auxin called CPIB, which also eliminates DR5 expression.

Figure 5:
FIG. 5. Wild type *Arabidopsis* seedlings were grown for four days in the dark in the presence of saturating ethylene (100 ppm) and either 0 or 10 µM pamoic acid after which it was determined whether aspects of the ethylene dependent seedling triple response were affected. Treatment resulted in elimination of the ethylene dependent apical hook and a significant increase in root length compared to seedlings that were not treated with pamoic acid. Similar effects were seen for the constitutive ethylene response mutant, ctrl-3.
Figure 6:
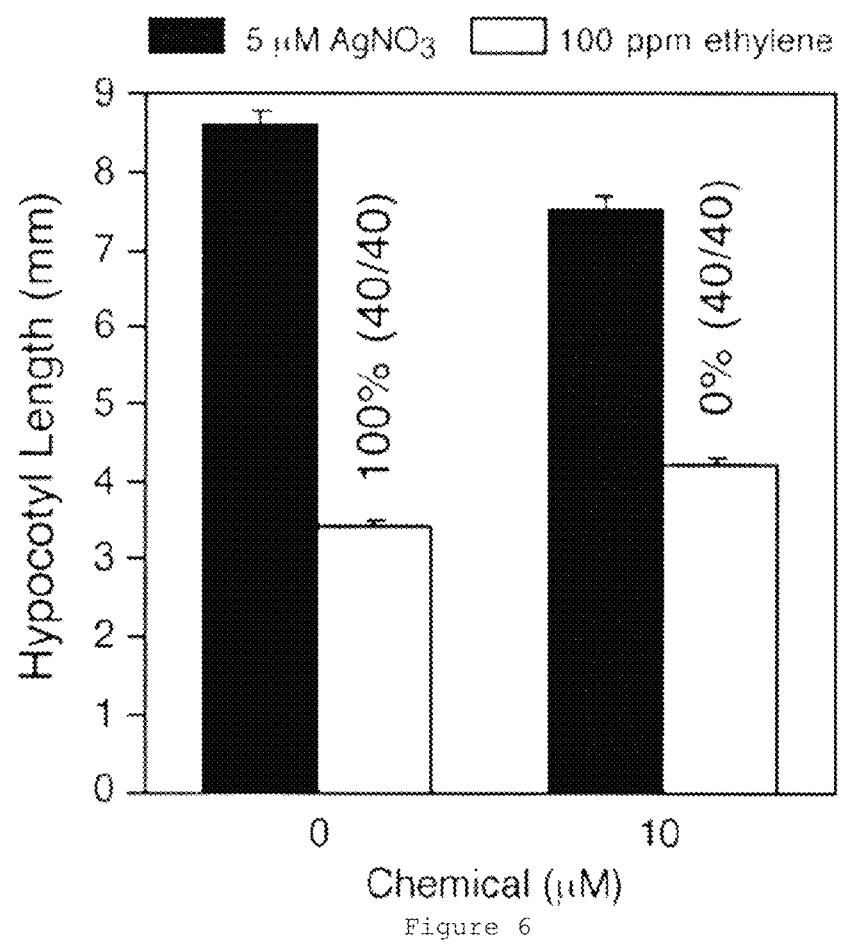
FIG. 6. Wild type *Arabidopsis* seedlings were grown for four days in the dark in the presence of either the ethylene perception inhibitor $AgNO_3$ or saturating ethylene (100 ppm) along with either 0 or 10 µM pamoic acid. Following this, hypocotyl length and number of seedlings presenting an ethylene dependent apical hook in the presence of saturating ethylene (shown as percentages) were determined (n=40).
Figure 7:
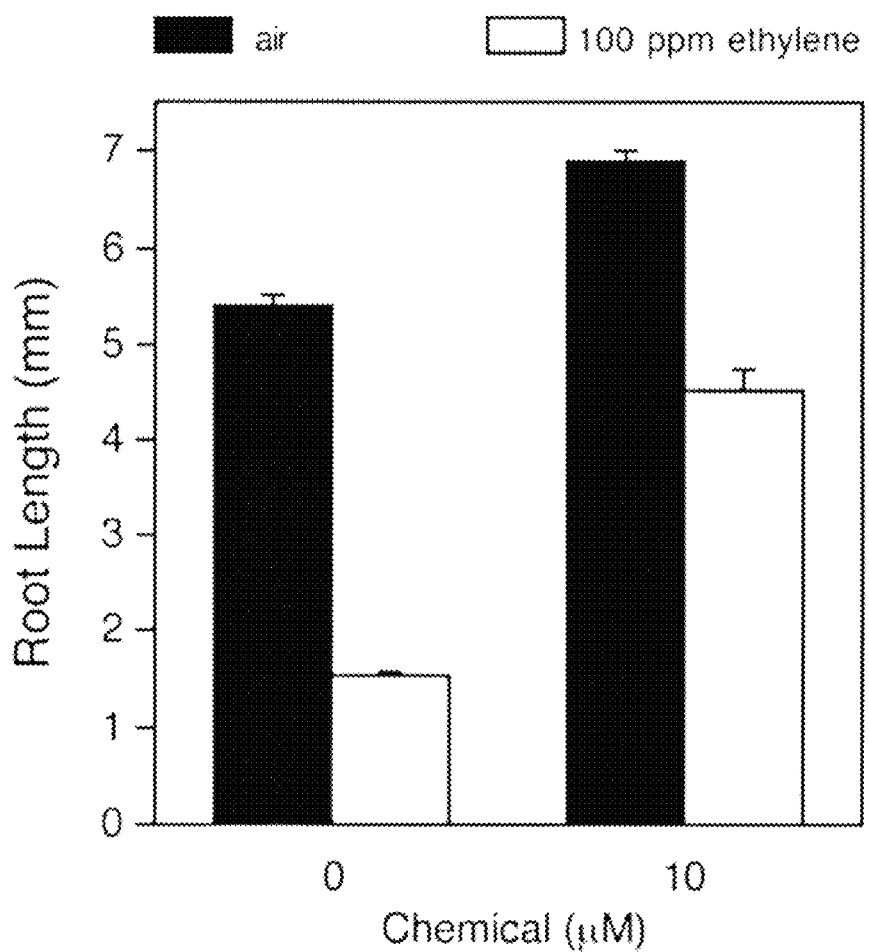
FIG. 7. Wild type *Arabidopsis* seedlings were grown for four days in the dark in the presence of either air or saturating ethylene (100 ppm) along with either 0 or 10 µM pamoic acid. Following this, root length was measured for each treatment (n=40).
Figure 8:
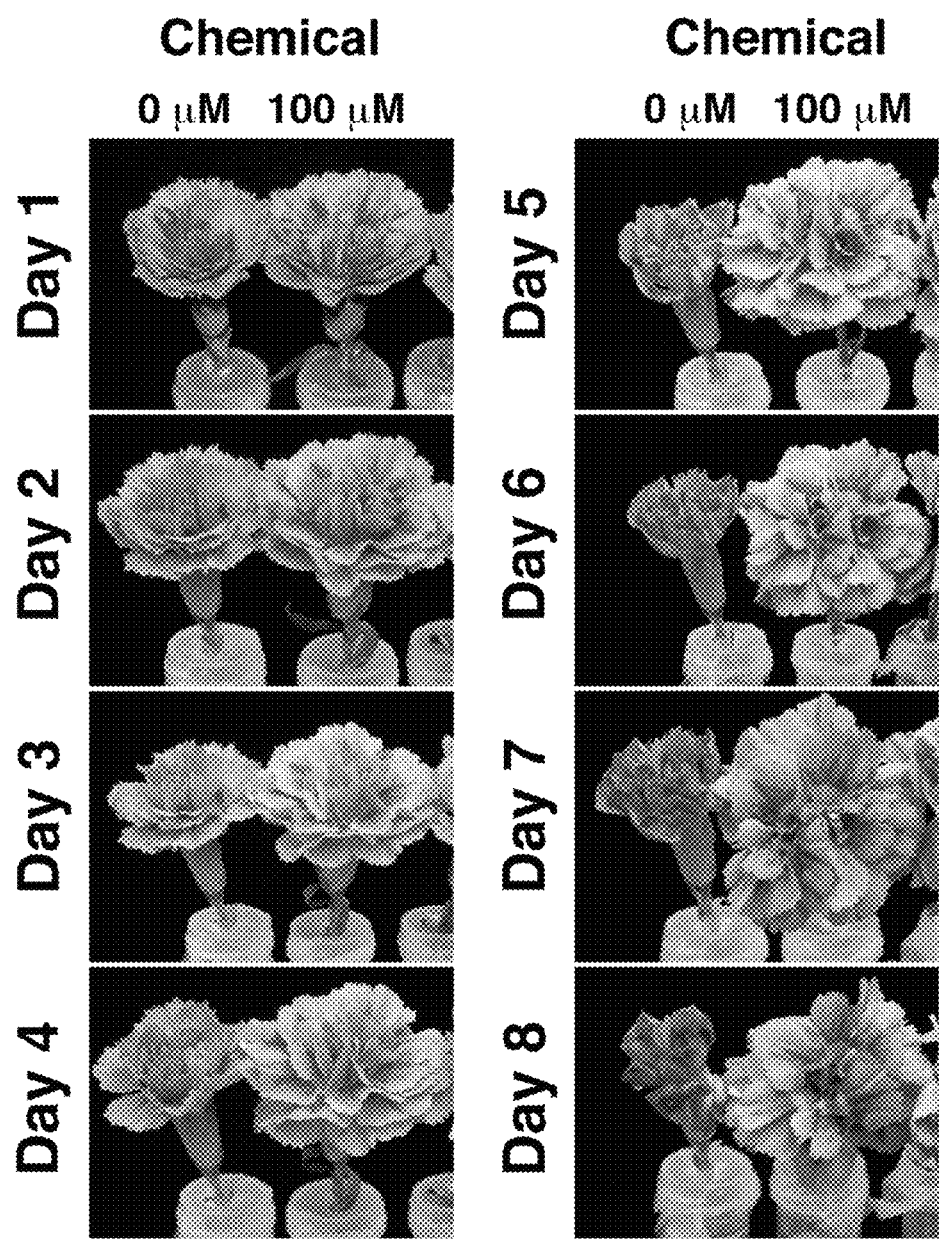
FIG. 8. Flowers of *Dianthus caryophyllus* (carnation) were harvested and immediately placed cut side down into either water or water supplemented with 50 µM pamoic acid. Samples were observed for development of symptoms of ethylene dependent flower senescence, including petal inrolling. Whereas untreated flowers showed the beginning signs of petal senescence by Day 4, flowers treated with pamoic acid had no evidence of petal inrolling or petal senescence even after Day 8.
Figure 9:
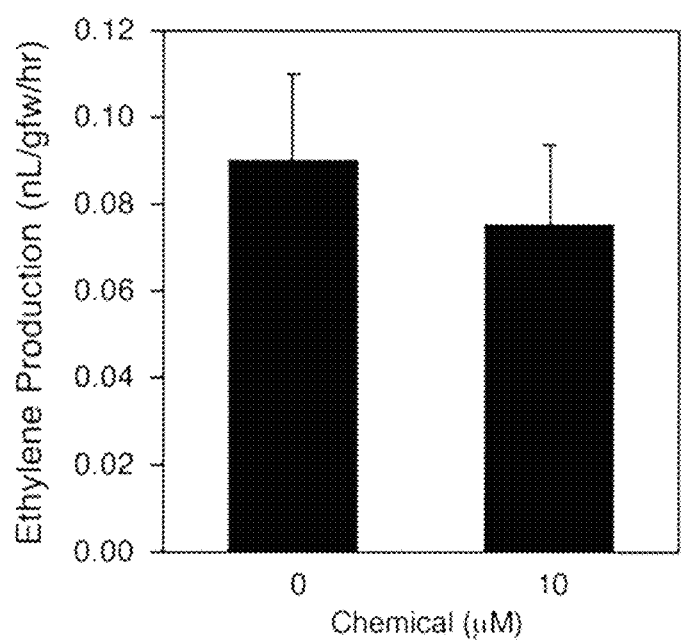
FIG. 9 shows a measure of ethylene production by *Arabidopsis* seedlings in the absence or presence of pamoic acid.

FIGS. 5-7 shows the effects of pamoic acid on the manifestation of an ethylene dependent growth phenotype known as the triple response. This is a dark phenotype that results in severe stunting of shoot and root growth along with a pronounced apical hook in the presence of saturating ethylene. This phenotype is ultimately conditioned by auxin acting through ethylene. Consequently, based on this and other results, the data show that pamoic acid functions as an anti-auxin that also happens to block ethylene phenomena due to the synergy between the two. FIG. 5 represents a mutant that has constitutive ethylene signaling (ctr1) and FIGS. 6 and 7 represents wild type treated with ethylene+/− PA. In all cases, PA strictly blocks several ethylene response phenomena including apical hook formation and root growth inhibition.

FIG. 10 shows that growth of seedlings on increasing amounts of PA results in progressively shorter roots, which is consistent with blocking detection of a hormone that is required for growth. Panel 10A shows that high concentrations of PA almost completely block root growth. This is not a toxicity issue in due to the data in panels 10B and C. In panel 10B, seedlings were grown in the absence or presence of a highly inhibitory amount of NAA. A subset of these seedlings also had PA added to them. The data shows that PA effectively prevented the inhibitory effects of NAA, since PA+NAA treated roots were nearly double the length of NAA treated roots. In panel 10C, the data show that treatment of wild type roots with PA completely destroys the gravitropic response of seedling roots. Gravitropism is a well know auxin dependent phenomenon. The data show that both roots and shoots become agravitropic in the presence of PA, which is consistent with PA being an anti-auxin. Interestingly, ornamental horticultural phenomena such as weeping (e.g. weeping cherries) is an agravitropic phenomenon, suggesting that PA can be used to modulate such responses.

FIG. 11 shows the PA is structurally similar to that of to molecules of NAA linked at $C_4$ of NAA. Accordingly, it is likely that PA is a competitive inhibitor of NAA and auxin action since it is ecpted to prevent auxins from binding to their receptor.

FIG. 12 shows the effect of PA on gene expression. Since PA reduces ethylene response, it was natural to assume that it would also reduce ethylene mediated gene expression. In contrast, several ethylene inducible genes, as shown in panel 12A, are normally upregulated following ethylene treatment even in the presence of PA. PA was then tested on gene expression that was dependent on auxin and ethylene. Surprisingly, expression of two genes that require both ethylene and auxin for induction was extremely reduced in the presence of PA, suggesting that PA is targeting auxin signaling.

A number of embodiments of the invention have been described. Nevertheless, it will be understood that various modifications may be made without departing from the spirit and scope of the invention. Accordingly, other embodiments are within the scope of the following claims.

What is claimed is:

1. A method of preserving cut flowers comprising contacting cut flowers with a composition comprising pamoic acid or a derivative thereof, in an effective amount to preserve cut flowers.

2. The method of claim 1, wherein the pamoic acid has a general structure as shown in Formula I or Formula II:

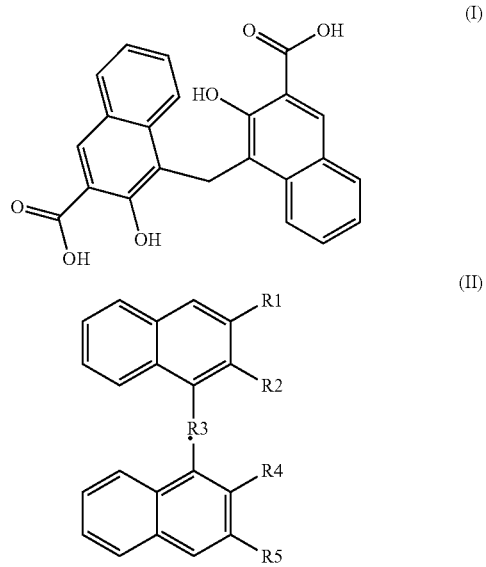

wherein R1 and R5, which may be the same or different, are $COOR_6$, in which $R_6$ is H or a straight or branched, saturated or unsaturated alkyl chain, with from 1 to 5 carbons atoms; R2 and R4, which may be the same or different, are H or OH; and R3 is —$(CH_2)_n$—, wherein n is an integer of 1.

3. The method of claim 2, wherein $R_1$ and $R_5$ are —$COOCH(CH_3)_2$; $R_2$ and $R_4$ are —OH; and is $R_3$ —$CH_2$—.

* * * * *

UNITED STATES PATENT AND TRADEMARK OFFICE
CERTIFICATE OF CORRECTION

PATENT NO. : 9,877,479 B2
APPLICATION NO. : 15/149899
DATED : January 30, 2018
INVENTOR(S) : Paul Brian Larsen Page 1 of 1

It is certified that error appears in the above-identified patent and that said Letters Patent is hereby corrected as shown below:

In Column 10:

Claim 2, Line 30, "carbons" should be –carbon–; and,

Claim 3, Line 34, "and is $R_3$" should be –and $R_3$ is–.

Signed and Sealed this
Seventeenth Day of April, 2018

Andrei Iancu
*Director of the United States Patent and Trademark Office*